(12) United States Patent
Kiselev et al.

(10) Patent No.: US 10,125,170 B2
(45) Date of Patent: *Nov. 13, 2018

(54) BIOACTIVE PEPTIDE COMPLEXES

(71) Applicant: Alloferon Inc., Seongnam-si (KR)

(72) Inventors: Oleg Ivanovich Kiselev, St. Petersburg (RU); Feliks Ivanovich Ershov, Moscow (RU)

(73) Assignee: Alloferon Inc., Seongnam-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/291,519

(22) Filed: Oct. 12, 2016

(65) Prior Publication Data

US 2017/0058000 A1 Mar. 2, 2017

Related U.S. Application Data

(62) Division of application No. 14/401,353, filed as application No. PCT/RU2012/000405 on May 21, 2012, now Pat. No. 9,499,585.

(51) Int. Cl.
| | | |
|---|---|---|
| *A61K 38/00* | (2006.01) | |
| *A61K 38/08* | (2006.01) | |
| *C07K 7/08* | (2006.01) | |
| *C07K 7/06* | (2006.01) | |
| *C07K 7/64* | (2006.01) | |

(52) U.S. Cl.
CPC ............. *C07K 7/08* (2013.01); *C07K 7/06* (2013.01); *A61K 38/00* (2013.01)

(58) Field of Classification Search
CPC .......... A61K 38/00; A61K 38/08; C07K 7/08; C07K 7/06; C07K 7/64
USPC ........................................................ 530/327
See application file for complete search history.

(56) References Cited

U.S. PATENT DOCUMENTS

2011/0070376 A1 3/2011 Wales et al.

FOREIGN PATENT DOCUMENTS

| RU | 2172322 C1 | 8/2001 |
| RU | 2008/147686 A | 6/2010 |

OTHER PUBLICATIONS

Janicka, Anna et al., "Coordination ability of alloferon peptide towards Cu 2+ ions", *18th Polish Peptide Symposium*, Wroclaw, pp. 112-113, Sep. 4-8, 2008.(Abstract Only).

Kowalik-Jankowski, Teresa et al., "Mononuclear copper(II) complexes of alloferons 1 and 2: A combined potentiometric and spectroscopic studies", *Journal of Inorganic Biochemistry*, vol. 103, Issue 1, pp. 135-142, Jan. 2009. (Abstract Only).

Matera, Agnieszka et al., "The role of the histidine residue in the coordination abilities of peptides with a multi-histidine sequence towards copper(II) ions", *Polyhedron* vol. 27, Issue 6, pp. 1539-1555, Apr. 25, 2008. (Abstract Only).

International Search Report for PCT Application No. PCT/RU2012/000405 prepared by the Russian Patent Office, dated Feb. 21, 2013. (English Translation Included).

Isied et al., "Specific Peptide Sequences for Metal Ion Coordination. 1. Solid-Phase Synthesis of cyclo-(Gly-His)3", *JACS*, vol. 104, Issue 9, pp. 2632-2634, 1982.

*Primary Examiner* — Julie Ha

(74) *Attorney, Agent, or Firm* — Chalin A. Smith; Smith Patent, LLC

(57) ABSTRACT

Herein disclosed are bioactive peptides and proteins having immunomodulating and antiviral activity, more particularly histidine-rich bioactive peptide complexes having the following structural formula (SEQ ID NO: 29):

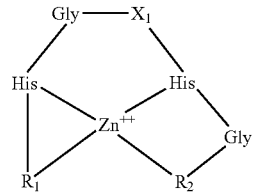

wherein: $X_1$ is preferably absent or is selected from among Gln, Ser, Asn, Val, Ala, Phe, and Asp, and $R_1$ and $R_2$ are peptide chains optionally contain the amino acid residues His and/or Cys that interact with transition metal ions. Whereas $R_1$ is preferably selected from among His-Gly-Val-Ser-Gly(SEQ ID NO: 30), CysVal-Val-Thr-Gly- (SEQ ID NO: 31), Cys-Gly-, Val-Ser-Gly-, and His-Gly- or alternatively is absent, $R_2$ is preferably selected from among -Val-His-Gly, -Val-Phe-Val, -Val-His, -Val-Asp or alternatively is absent. Such histidine-rich peptide complexes, primarily alloferon family peptides such as Alloferon-1 (SEQ ID NO: 1) with Zn ions, enable the creation of drugs with a targeted mechanism of action, and the design thereof with regard to understanding of drug target structure.

9 Claims, 9 Drawing Sheets

Specification includes a Sequence Listing.

Fig. 1: Analysis of the consensus sequences of alloferon family peptides.

```
                        1              14
ALLOFERON 1    (1) HGVSGHGQ-HGVHG
ALLOFERON 10   (1) CVVSGHGS-HGVFV
ALLOFERON 11   (1) --ISGHGQ-HGVP-
ALLOFERON 12   (1) ---CGHGN-HGVH-
ALLOFERON 13   (1) IVARIHGQNHGL--
ALLOFERON 14   (1) HGSDGHGVQHG---
ALLOFERON 15   (1) ---FGHG--HGV--
ALLOFERON 16   (1) -----HGN-HGVLA
ALLOFERON 17   (1) HGDSGHGQ-HGVD-
ALLOFERON 18   (1) -----HG--HGVPL
ALLOFERON 19   (1) ---SGHGAVHGVM-
ALLOFERON 2    (1) -GVSGHGQ-HGVHG
ALLOFERON 20   (1) YAMSGHG--HGVFI
ALLOFERON 3    (1) --VSGHGQ-HGVH-
ALLOFERON 4    (1) ---SGHGQ-HGV--
ALLOFERON 5    (1) PSLTGHGF-HGVYD
ALLOFERON 6    (1) FIVSAHGD-HGV--
ALLOFERON 7    (1) ----THGQ-HGV--
ALLOFERON 8    (1) ---HGHGV-HG---
ALLOFERON 9    (1) -LASLHGQ-HGV--
GEMAGGLUTIN 377-388 (1) HGYISHGA-HGV--
    CONSENSUS  (1)   SGHGQ HGV
```

GAP OPENING PENALTY = 6
GAP EXTENSION PENALTY = 0.05
GAP SEPARATION PENALTY RANGE = 8
RF FOR CONSENSUS = 0.5

Fig. 1: (Continued).

```
                            1              14
   ALLOFERON 1    (1) HGVSGHGQ-HGVHG
   ALLOFERON 10   (1) CVVTGHGS-HGVFV
   ALLOFERON 11   (1) --SGHGQ-HGVP-
   ALLOFERON 12   (1) ---CGHGN-HGVH-
   ALLOFERON 13   (1) IVARIHGQNHGI--
   ALLOFERON 14   (1) HGSDGHGVQHG---
   ALLOFERON 15   (1) ---FGHG--HGV--
   ALLOFERON 16   (1) -----HGN-HGVLA
   ALLOFERON 17   (1) HGDSGHGQ-HGVD-
   ALLOFERON 18   (1) -----HG--HGVPL
   ALLOFERON 19   (1) ---SGHGAVHGVM-
   ALLOFERON 2    (1) -GVSGHGQ-HGVHG
   ALLOFERON 20   (1) YAMSGHG--HGVFI
   ALLOFERON 3    (1) --VSGHGQ-HGVH-
   ALLOFERON 4    (1) ---SGHGQ-HGV--
   ALLOFERON 5    (1) PSVTGHGF-HGVYD
   ALLOFERON 6    (1) FIVSAHGD-HGV--
   ALLOFERON 7    (1) ----THGQ-HGV--
   ALLOFERON 8    (1) ---HGHGV-HG---
   ALLOFERON 9    (1) -LASLHGQ-HGV--
GEMAGGLUTIN 377-388 (1) HGYVSHGA-HGV--
     CONSENSUS   (1)  VSGHGQ HGV
     GAP OPENING PENALTY              = 6
     GAP EXTENSION PENALTY            = 0.05
     GAP SEPARATION PENALTY RANGE     = 8
     RF FOR CONSENSUS                 = 0.3
```

Fig. 1: (Continued).

```
                              1              14
ALLOFERON 1    (1) -HGVSGHGQHGVHG
ALLOFERON 10   (1) -CVVTGHGSHGVFV
ALLOFERON 11   (1) ---ISGHGQHGVP-
ALLOFERON 12   (1) ----CTHGNHGVH-
ALLOFERON 13   (1) IVARIHGQNHGI--
ALLOFERON 14   (1) HGSDGHGVQHG---
ALLOFERON 15   (1) -----FGHGHGV--
ALLOFERON 16   (1) ------HGNHGVLA
ALLOFERON 17   (1) -HGDSGHGQHGVD-
ALLOFERON 18   (1) -------HGHGVPL
ALLOFERON 19   (1) ---SGHGAVHGVM-
ALLOFERON 2    (1) --GVSGHGQHGVHG
ALLOFERON 20   (1) --YAMSGHGHGVFI
ALLOFERON 3    (1) ---VSGHGQHGVH-
ALLOFERON 4    (1) ----SGHGQHGV--
ALLOFERON 5    (1) -PSLTGHGFHGVYD
ALLOFERON 6    (1) -FIVSAHGDHGV--
ALLOFERON 7    (1) -----THGQHGV--
ALLOFERON 8    (1) ----HGHGVHG---
ALLOFERON 9    (1) --LASLHGQHGV--
GEMAGGLUTIN 377-388 (1) -HGYISHGAHGV--
    CONSENSUS  (1)     SGHGQHGV
```

| | |
|---|---|
| GAP OPENING PENALTY | = 10 |
| GAP EXTENSION PENALTY | = 0.05 |
| GAP SEPARATION PENALTY RANGE | = 8 |
| RF FOR CONSENSUS | = 0.5 |

Computer model of polypeptide A1.

Theoretically possible variants for the structure of A1 – $Zn^{++}$ complexes.

Fig. 4: Kinetics of alloferon A1 binding with $Zn^{++}$, by light scattering.
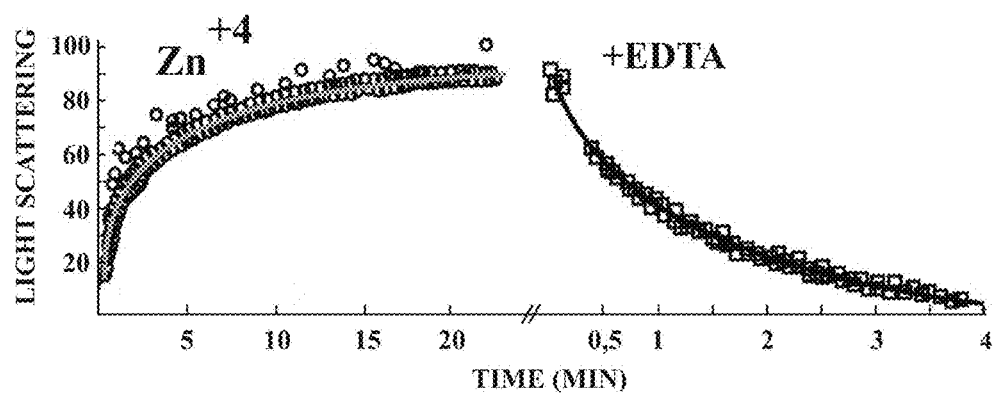

Fig. 5: Review of peptide A1 binding with HiTrap sorbent equilibrated with $Ni^{++}$.
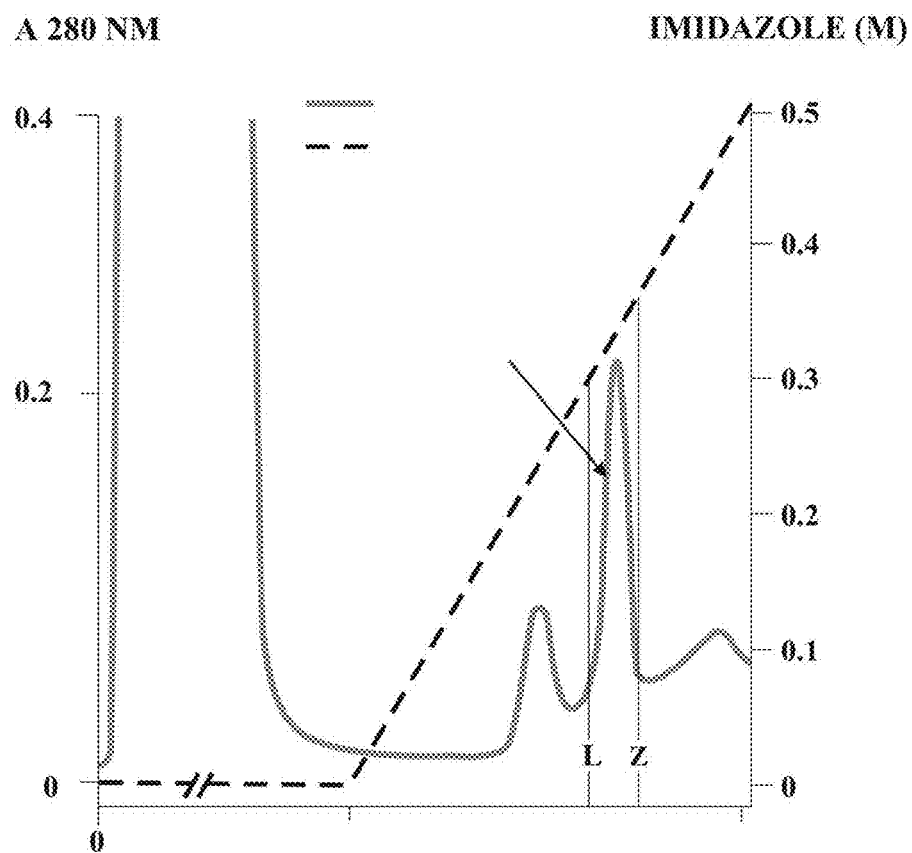

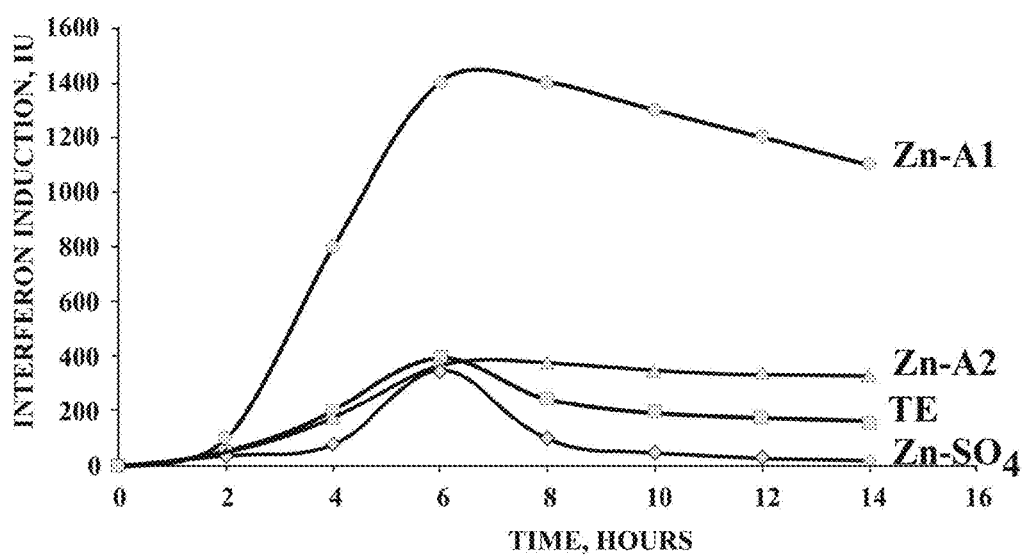
Fig. 6: Induction of type I interferons.

Fig. 7: The protective effect of tested products in lethal influenza infection in mice
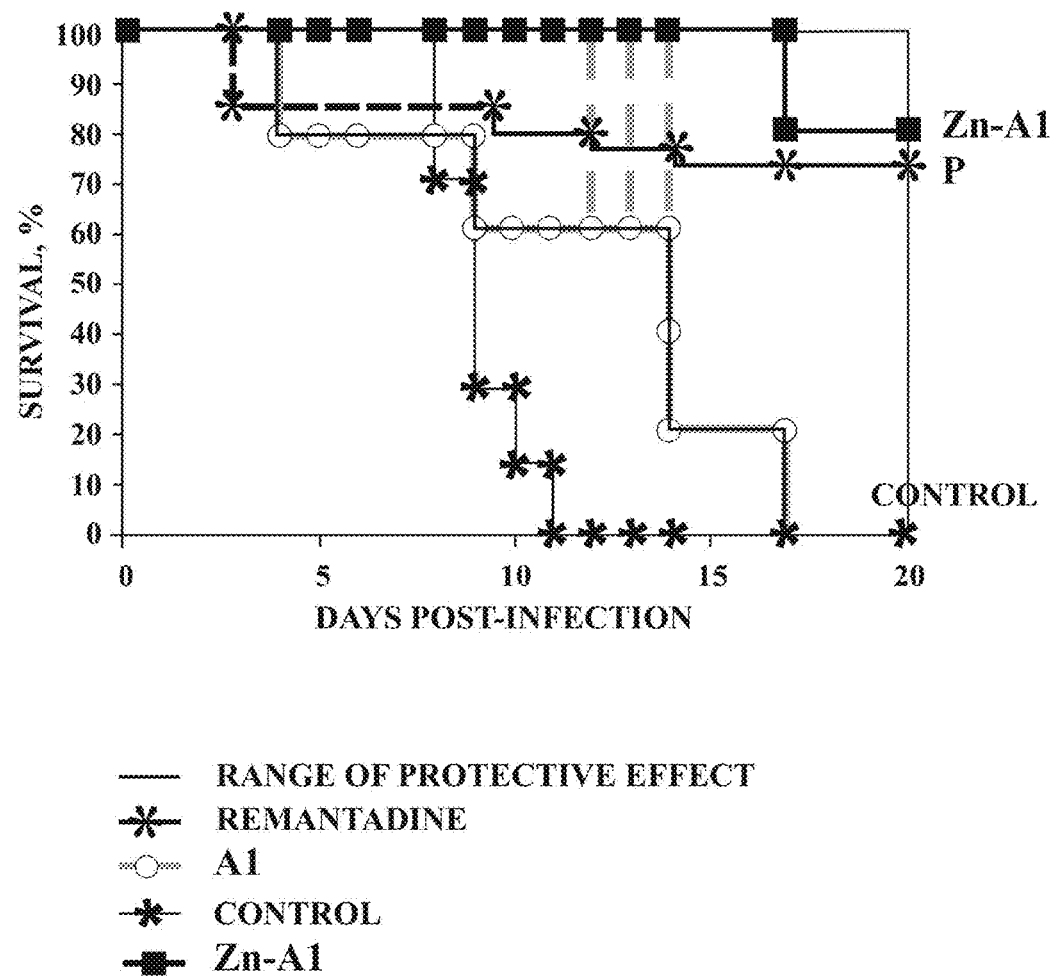

SEQUENCE LISTING

```
<160> NUMBER OF SEQ ID NOS: 33

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Alloferon 1

<400> SEQUENCE: 1

His Gly Val Ser Gly His Gly Gln His Gly Val His Gly
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Alloferon 10

<400> SEQUENCE: 2

Cys Val Val Thr Gly His Gly Ser His Gly Val Phe Val
1               5                   10
```

```
<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Alloferon 11

<400> SEQUENCE: 3

Ile Ser Gly His Gly Gln His Gly Val Pro
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Alloferon 12

<400> SEQUENCE: 4

Cys Gly His Gly Asn His Gly Val His
1               5

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Alloferon 13

<400> SEQUENCE: 5

Ile Val Ala Arg Ile His Gly Gln Asn His Gly Leu
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Alloferon 14

<400> SEQUENCE: 6

His Gly Ser Asp Gly His Gly Val Gln His Gly
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Alloferon 15

<400> SEQUENCE: 7

Phe Gly His Gly His Gly Val
1               5
```

```
<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Alloferon 16

<400> SEQUENCE: 8

His Gly Asn His Gly Val Leu Ala
1               5

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Alloferon 17

<400> SEQUENCE: 9

His Gly Asp Ser Gly His Gly Gln His Gly Val Asp
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Alloferon 18

<400> SEQUENCE: 10

His Gly His Gly Val Pro Leu
1               5

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Alloferon 19

<400> SEQUENCE: 11

Ser Gly His Gly Ala Val His Gly Val Met
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Alloferon 2

<400> SEQUENCE: 12

Gly Val Ser Gly His Gly Gln His Gly Val His Gly
1               5                   10
```

```
<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Alloferon 20

<400> SEQUENCE: 13

Tyr Ala Met Ser Gly His Gly His Gly Val Phe Ile
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Alloferon 3

<400> SEQUENCE: 14

Val Ser Gly His Gly Gln His Gly Val His
1               5                   10

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Alloferon 4

<400> SEQUENCE: 15

Ser Gly His Gly Gln His Gly Val
1               5

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Alloferon 5

<400> SEQUENCE: 16

Pro Ser Leu Thr Gly His Gly Phe His Gly Val Tyr Asp
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Alloferon 6

<400> SEQUENCE: 17

Phe Ile Val Ser Ala His Gly Asp His Gly Val
```

```
1               5              10
```

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Alloferon 7

<400> SEQUENCE: 18

Thr His Gly Gln His Gly Val
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Alloferon 8

<400> SEQUENCE: 19

His Gly His Gly Val His Gly
1               5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Alloferon 9

<400> SEQUENCE: 20

Leu Ala Ser Leu His Gly Gln His Gly Val
1               5                  10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Gemagglutin

<400> SEQUENCE: 21

His Gly Tyr Thr Ser His Gly Ala His Gly Val
1               5                  10

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(5)
<223> OTHER INFORMATION: Any naturally occurring amino acid
<220> FEATURE:

```
<221> NAME/KEY: MOD_RES
<222> LOCATION: (8)..(9)
<223> OTHER INFORMATION: Any naturally occurring amino acid
<220> FEATURE:
<221> NAME/KEY: MOD_RES
<222> LOCATION: (12)..(14)
<223> OTHER INFORMATION: Any naturally occurring amino acid

<400> SEQUENCE: 22

Xaa Xaa Xaa Xaa Xaa His Gly Xaa Xaa His Gly Xaa Xaa Xaa
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid or not present
<220> FEATURE:
<221> NAME/KEY: MOD_RES
<222> LOCATION: (8)..(8)
<223> OTHER INFORMATION: Any amino acid or not present
<220> FEATURE:
<221> NAME/KEY: MOD_RES
<222> LOCATION: (11)..(13)
<223> OTHER INFORMATION: Any amino acid or not present
<220> FEATURE:
<223> OTHER INFORMATION: See specification as filed for detailed
      description of substitutions and preferred embodiments

<400> SEQUENCE: 23

Xaa Xaa Xaa Xaa Xaa His Gly Xaa His Gly Xaa Xaa Xaa
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: His, Cys, Ile, Tyr, Pro, Phe or not present
<220> FEATURE:
<221> NAME/KEY: MOD_RES
<222> LOCATION: (2)..(2)
<223> OTHER INFORMATION: Gly, Val, Ala, Ser, Ile, Leu or not present
<220> FEATURE:
<221> NAME/KEY: MOD_RES
<222> LOCATION: (3)..(3)
<223> OTHER INFORMATION: Val, Ile, Ala, Ser, Asp, Met, Leu, Tyr or not
      present
<220> FEATURE:
<221> NAME/KEY: MOD_RES
<222> LOCATION: (4)..(4)
<223> OTHER INFORMATION: Ser, Thr, Cys, Arg, Asp, Phe, His or not
      present
<220> FEATURE:
<221> NAME/KEY: MOD_RES
<222> LOCATION: (5)..(5)
<223> OTHER INFORMATION: Gly, Ile, Ala, Thr, Leu, Ser or not present
<220> FEATURE:
<221> NAME/KEY: MOD_RES
<222> LOCATION: (8)..(8)
<223> OTHER INFORMATION: Gln, Ser, Asn, Val, Ala, Phe, Asp or not
      present
<220> FEATURE:
<221> NAME/KEY: MOD_RES
```

```
<222> LOCATION: (9)..(9)
<223> OTHER INFORMATION: Asn, Gln, Val or not present
<220> FEATURE:
<221> NAME/KEY: MOD_RES
<222> LOCATION: (12)..(12)
<223> OTHER INFORMATION: Val, Leu or not present
<220> FEATURE:
<221> NAME/KEY: MOD_RES
<222> LOCATION: (13)..(13)
<223> OTHER INFORMATION: His, Phe, Pro, Leu, Asp, Met, Tyr or not
      present
<220> FEATURE:
<221> NAME/KEY: MOD_RES
<222> LOCATION: (14)..(14)
<223> OTHER INFORMATION: Gly, Val, Ala, Leu, Ile, Asp or not present
<220> FEATURE:
<223> OTHER INFORMATION: See specification as filed for detailed
      description of substitutions and preferred embodiments

<400> SEQUENCE: 24

Xaa Xaa Xaa Xaa Xaa His Gly Xaa Xaa His Gly Xaa Xaa Xaa
1               5                   10

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 25

Ser Gly His Gly Gln His Gly Val
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 26

Val Ser Gly His Gly Gln His Gly Val
1               5

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

His Val Ser His Gly Gln His Gly Val His Gly
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

His Gly Val Ser Gly His Gly Gln His Gly Val Gly
1               5                   10
```

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(6)
<223> OTHER INFORMATION: This region may encompass "His Gly Val Ser
      Gly," "Cys Val Val Thr Gly," "Cys Gly," "His Gly Ser Asp Gly,"
      "Gly His Gly Asp Ser Gly," "Val Ser Gly," or "His Gly," wherein
      some or all positions may be absent
<220> FEATURE:
<221> NAME/KEY: MOD_RES
<222> LOCATION: (9)..(9)
<223> OTHER INFORMATION: Gln, Ser, Asn, Val, Ala, Phe, Asp or not
      present
<220> FEATURE:
<221> NAME/KEY: MISC_FEATURE
<222> LOCATION: (12)..(14)
<223> OTHER INFORMATION: This region may encompass "Val His Gly," "Val
      Phe Val," "Val His," or "Val Asp," wherein some or all positions
      may be absent
<220> FEATURE:
<223> OTHER INFORMATION: See specification as filed for detailed
      description of substitutions and preferred embodiments

<400> SEQUENCE: 29

Xaa Xaa Xaa Xaa Xaa Xaa His Gly Xaa His Gly Xaa Xaa Xaa
1               5                   10

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

His Gly Val Ser Gly
1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Cys Val Val Thr Gly
1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

His Gly Ser Asp Gly
1               5

```
<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly His Gly Asp Ser Gly
1               5
```

BIOACTIVE PEPTIDE COMPLEXES

PRIORITY

This application is a divisional of U.S. application Ser. No. 14/401,353 filed Nov. 14, 2014, which, in turn, corresponds to the U.S. National Phase of International Application No. PCT/RU2012/000405 filed May 21, 2012, the entire contents of which are hereby incorporated by reference.

SEQUENCE LISTING

The instant application contains a Sequence Listing that has been submitted in ASCII format via EFS-Web and is hereby incorporated by reference in its entirety. Said ASCII copy, created on May 12, 2015, is named LNK_157US_SL.txt and is 10,981 bytes in size.

FIELD OF THE PRESENT INVENTION

The present invention refers to proteins and bioactive peptides with immunomodulating and antiviral activity.

BACKGROUND OF THE PRESENT INVENTION

Peptide, polypeptide and protein-based compounds used in medicine as antiviral drugs are known. Among type I interferon inducers (IFI) they are known as high-molecular compounds [F. I. Yershov, O. I. Koselev. Interferons and their inducers from the molecule to the drug—, M.: Publ. House. Geotar-Media, 2005-P. 356], [Berg K., Bolt G., Andersen H., Owen T C. Zink potentiates the antiviral action of human IFN-alpha tenfold. J. Interferon Cytokine Res, 2001, July; 21(7):471-4], as low-molecular inducers. From the latter, first of all, native drug cycloferon and American drug imiquimod should be noted. These drugs refer to acridone and benzimidazole derivatives, respectively. For imiquimod and close derivatives, Toll-like type of receptors is known, with which this group of drugs interacts causing IFN-α synthesis induction in various cells [F. I. Yershov., O. I. Kiselev. Interferons and their inducers (from the molecule to the drug) M.: Publ. House. Geotar-Media, 2005.-P. 356].

Bioactivity of low-molecular peptides is widely known. First of all, this refers to animal and plant origin peptides with antibacterial activity [Boman H. Peptide antibiotics and their role in innate immunity. Anu. Rev. of Immunol., 1995, Vol. 13, p. 61-92]. However, a number of peptides possessing direct antiviral and antitumour action has been described [Akiyama N., Hijikata M., Kobayashi A., Yamori T., Tsuruo T., Natori S. Anti-tumor effect of N-β-alanyl-5-S-glutathionyl dihydroxyphenylalanine (5-S-GAD) a novel anti-bacterial substance from an insect. Anticancer Research, 2000, Vol. 20, p. 357-362].

Peptides of amphibians and insects take a special place here [Bulet P., Hetru C., Diamarcq J., Hoffmann D. Antimicrobial peptides in insects: structure and function. Devel. Comp. Immunol., 1999, Vol. 23, p. 329-344, Chinchar V. G., Wang J., Murti G., Carey C., Rolling-Smith L. Inactivation of frog virus 3 and channel catfish virus by esculentin-2P and ranatuerin-2P, two antimicrobial peptides isolated from frog skin. Virology, 2001, Vol. 288, p. 351-357].

Immunomodulating peptides—alloferons are known (patent of the RF U.S. Pat. No. 2,172,322). Treatment of viral infections is the main area of application for alloferons. Alloferons are the closest analogues of the present invention regarding chemical structure and mode of action.

It should be noted, that inventors of the patent U.S. Pat. No. 2,172,322 only consider variations of primary alloferon structure and do not place key value to histidine residues distribution.

Moreover, alloferons should be referred to quite "weak" interferon inducers, which is evident when comparing their activity with cycloferon.

At the same time, alloferons structure stands out with regular histidine residues arrangement and frequent glycine residues. Enhancement of alloferons structure is possible towards giving them tertiary structure elements, for instance, by introduction of metal ions.

Hemin-peptide and its pharmaceutically acceptable salts with virucidal and antiviral action, containing metal ions, where Zn, Cu, Fe, Mn can be used, is also known. (Patent of the RF U.S. Pat. No. 2,296,131). However, this compound refers to the second class of peptides and is not an immune modulator.

Peptide complexes with $Zn^{++}$ ion, with elements of organized tertiary structure and activity of first type interferon inducers, are not described in the literature.

Need for modification of histidine-containing peptides with $Zn^{++}$ ion is driven by the following causes:

1. Bioactive short peptides have disorganized type of secondary structure inevitably reducing their bioactivity, interactability with other macromolecules, metabolic stability.

2. Biological and pharmacological activity of peptides largely depends on transport efficiency to cells. Making peptide structure compact increases effectiveness of their translocation through membranes and, subsequently, pharmacological activity [Leng Q., Mixson J. Modified branched peptides with histidine-rich tail enhance in vitro gene transfection. Nucl. Acids. Res., 2005, Vol. 33, e40].

3. Formation of histidine-containing peptide complexes with $Zn^{++}$ ion results in fundamental changes of peptides properties, making them identical with domains of transcriptional activators of viruses and cells.

SUMMARY OF THE PRESENT INVENTION

The objective of the present invention is to develop peptide complexes organized in three-dimensional structure. The designed complexes possess high binding ability with other molecular groups and display wide spectrum of pharmacological action, including type I IFN induction and act on various levels of cellular functions, allowing to create new drugs for prevention and treatment of viral infections based on them.

The new family of bioactive peptides has been developed based on the known peptides, enriched with histidine residues, alloferons and their homologues using Zn-finger of protein domains with known functions as a prototype. Alloferons are used as a peptide matrix 6 to 35 amino acid residues long. In this way engineered peptides are able to form complexes with $Zn^{++}$ ion, creating oligomers and aggregates, and regarding structural and biological properties they meet the requirements of immune modulators.

Present peptide complexes have three-dimensional structure and are described by the following structural formula (SEQ ID NO: 23):

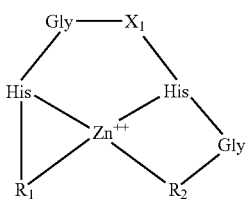

where: $X_1$ is absent or contains not less than 1 amino acid; and R1 and R2 are peptide chains containing amino acid residues that interact with transition metal ions, with R1 containing up to 5 amino acid residues or absent; R2 contains up to 3 amino acid residues or absent.

Ability of natural peptides, enriched with histidine residues, to bind with metal ions has been proved in a number of studies [Hua Zhao H., and Waite J. H. Proteins in Load-Bearing Junctions: The Histidine-Rich Metal-Binding Protein of Mussel Byssus, Biochemistry. 2006, 45(47): 14223-14231].

BRIEF DESCRIPTION OF THE FIGURES

Essence of invention is explained with the data from the schemes and figures:

FIG. 1. Consensus sequence analysis of alloferon family peptides. FIG. 1 discloses SEQ ID NOS 1-21, 25, 1-21, 26, 1-21, and 25, respectively, in order of appearance.

FIG. 2A discloses SEQ ID NO: 1.

FIG. 3A discloses SEQ ID NO 1 and FIG. 3B discloses SEQ ID NOS 28 and 28, respectively, in order of appearance.

FIG. 4. Binding kinetics of alloferon A1 with $Zn^{++}$ by light-scattering method.

FIG. 5. Peptide A1 binding analysis with $Ni^{++}$ balanced HiTrap adsorbent.

FIG. 6. Type I interferons induction.

FIG. 7. Protective effect of the studied drugs in case of lethal grippal infection in mice.

DETAILED DESCRIPTION OF THE PREFERRED EMBODIMENTS

Figure 2A:
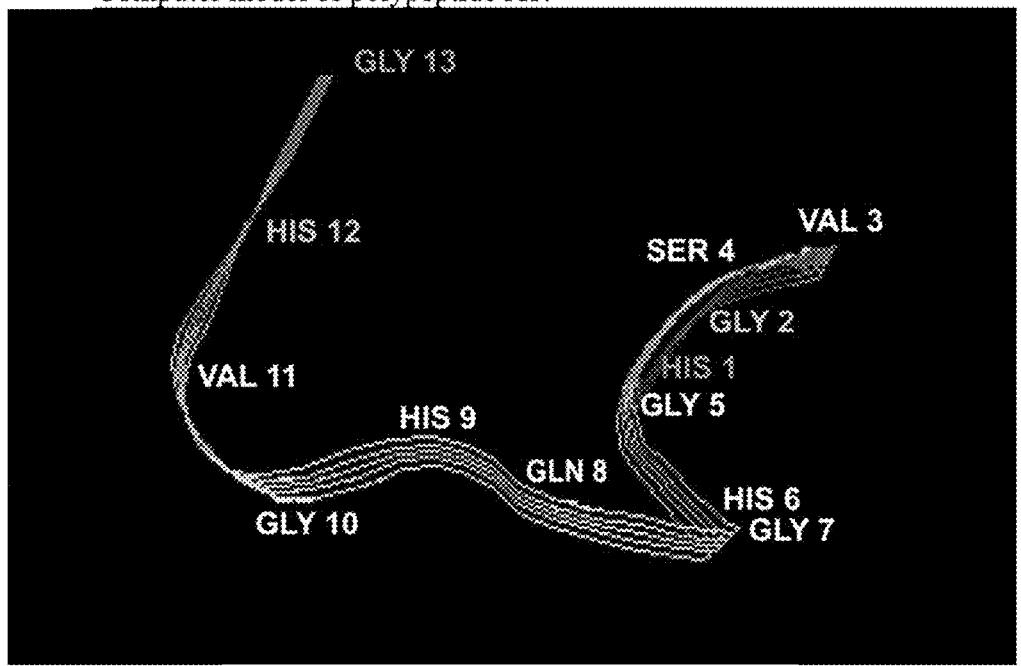
FIGS. 2A and 2B. A1 polypeptide computer model.

Alloferon 1 (SEQ ID NO 1) peptide, presented in the Table 2, has been used as a base structure during development of the present invention. Alloferon 1 was synthesized by solid-phase synthesis method and used to study bioactivity of the present peptides. The studies, the findings of which were presented in examples below, demonstrated that this peptide has ability to form complexes with transition metals, is interferon inducer and possesses antiviral activity.

Databases computer analysis of the proteins and peptides structure and properties found that this compound refers to the novel family of bioactive peptides. Histidine and glycine-rich polypeptides with introduced metal ions possess immune modulating and antiviral activity with zinc ions potentiating their bioactivity.

Synthesis of the present sequence of peptides has been performed in solid-phase peptides synthesis using Boc/Bzl strategies of phenyl acetamide methyl polymer (PAM). Peptides were isolated on Coupler-250 and Applied Biosystems 430A peptide synthesizers.

Tert-Butoxycarbonilamino group was used for temporary protection of α-amino groups removed with trifluoroacetic acid. Benzyl and acyl types safety groups have been used for suppression of lateral radicals of trifunctional amino acids: dinitrophenyl for histidine, mesitylenesulfonyl for arginine, 2-chlorbenzyloxycarbonyl for lysine, fromyl for tryptophan, 2,6-dychlorbenzyl for tyrosine, O-benzyl ethers for threonine and serine. Methionine was administered in condensation in the form of sulphoxy derivative.

Removal of temporary protection groups was performed with undiluted trifluoroacetic acid, and neutralization—by in situ method, adding N,N'-diisopropylethylamine at condensation stage directly into reaction mixture.

The program for addition of one amino acid residue during peptidyl-polymer chain elongation in an amount of total content of acylamino acid on the 0.2 mmol polymer is given in the table. Preactivation of carboxy component was performed within 30 minutes using hydroxybenzotriazole and diisopropylcarbodiimide. Under such conditions of synthesis in all the cases after addition of needed volume of amino acid residues, relevant to peptide fragment sequence, satisfactory peptidyl-polymer increment was reached.

Removal of side protection groups and peptide elimination from resin was performed under the action of anhydrous hydrogen fluoride in the presence of scavengers, mainly, m-cresol. During such treatment, all the side protection groups were removed and peptide was eliminated from high-molecular matrix, release time fluctuated from one to one and a half hour.

To prevent from adverse reactions during methionine-containing peptides synthesis, (in particular, sulphur alkylation with tert-butyl radical, and its partial oxidation during peptide chain elongation) methionine residues are smoothly added into peptidylpolymer sequence in the form of sulphoxy derivative, which at the end stages of peptide release was recovered to methionine. This recovery reaction had satisfactory results when treated with ammonium iodide or with completely released peptide, or at the stage, when peptide was still at the resin.

TABLE 1

Program for addition of one amino acid residue

| No. | Operation | Reagents | Repetition factor | Time, min | Reagents volume, mL |
|---|---|---|---|---|---|
| 1. | Removal of Rec-protection (release) | Trifluoroacetic acid | 1 | 2 | 5 |
| 2. | Metronomic release | Trifluoroacetic acid | 1 | 2 | 5 |
| 3. | Washing | Dymethylformamide | 3 | 1 | 10 |
| 4 | Condensation | 1.0 mmol of oxybenzotrisol ether of the relevant amino | 1 | 20 | 5 |

TABLE 1-continued

Program for addition of one amino acid residue

| No. | Operation | Reagents | Repetition factor | Time, min | Reagents volume, mL |
|---|---|---|---|---|---|
|  |  | acid derivative + Diisopropylethylamine (0.7 mmol in dymethylformamide) |  |  |  |
| 5. | Washing | Dymethylformamide | 3 | 1 | 10 |
| 6. | Washing | Methylene dichloride | 3 | 1 | 10 |
| 7. | Ninhydrin test* |  |  |  |  |

*condensation was repeated in case of positive ninhydrin test

All synthesized peptide drugs were purified using preparative reverse-phase liquid chromatography at the column Dynamax 60 A, 22.5×250 mm (liquid chromatograph Gilson, France) and are characterized by findings of hydrolysate peptides amino acid analysis after hydrolysis with methanesulfonic acid in the presence of tryptamine (amino acid analyzer Alpha Plus, LKB, Sweden).

EXAMPLES

The following examples prove the possibility to accomplish the object of invention.

Example 1. Analysis of Structure and Consensus Sequences of Alloferon Family Peptides BioEdit v.7.09 Ibis Biosciences (US) software was used for consensus sequence analysis of alloferon peptides families. Alloferon amino acid sequences homology is presented in the table 2.

TABLE 2

Alloferon sequence homology

| | peptide | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| SEQ ID NO 1 Alloferon 1 | His | Gly | Val | Ser | Gly | His | Gly | Gln | | His | Gly | Val | His | Gly |
| SEQ ID NO 2 Alloferon 10 | Cys | Val | Val | Thr | Gly | His | Gly | Ser | | His | Gly | Val | Phe | Val |
| SEQ ID NO 3 Alloferon 11 | | | Ile | Ser | Gly | His | Gly | Gln | | His | Gly | Val | Pro | |
| SEQ ID NO 4 Alloferon 12 | | | | Cys | Gly | His | Gly | Asn | | His | Gly | Val | His | |
| SEQ ID NO 5 Alloferon 13 | Ile | Val | Ala | Arg | Ile | His | Gly | Gln | Asn | His | Gly | Leu | | |
| SEQ ID NO 6 Alloferon 14 | His | Gly | Ser | Asp | Gly | His | Gly | Val | Gln | His | Gly | | | |
| SEQ ID NO 7 Alloferon 15 | | | | Phe | Gly | His | Gly | | | His | Gly | Val | | |
| SEQ ID NO 8 Alloferon 16 | | | | | | His | Gly | Asn | | His | Gly | Val | Leu | Ala |
| SEQ ID NO 9 Alloferon 17 | His | Gly | Asp | Ser | Gly | His | Gly | Gln | | His | Gly | Val | Asp | |
| SEQ ID NO 10 Alloferon 18 | | | | | | His | Gly | | | His | Gly | Val | Pro | Leu |
| SEQ ID NO 11 Alloferon 19 | | | | Ser | Gly | His | Gly | Ala | Val | His | Gly | Val | Met | |
| SEQ ID NO 12 Alloferon 2 | | Gly | Val | Ser | Gly | His | Gly | Gln | | His | Gly | Val | His | Gly |
| SEQ ID NO 13 Alloferon 20 | Tyr | Ala | Met | Ser | Gly | His | Gly | | | His | Gly | Val | Phe | Ile |
| SEQ ID NO 14 Alloferon 3 | | | Val | Ser | Gly | His | Gly | Gln | | His | Gly | Val | His | |
| SEQ ID NO 15 Alloferon 4 | | | | Ser | Gly | His | Gly | Gln | | His | Gly | Val | | |
| SEQ ID NO 16 Alloferon 5 | Pro | Ser | Leu | Thr | Gly | His | Gly | Phe | | His | Gly | Val | Tyr | Asp |
| SEQ ID NO 17 Alloferon 6 | Phe | Ile | Val | Ser | Ala | His | Gly | Asp | | His | Gly | Val | | |
| SEQ ID NO 18 Alloferon 7 | | | | | Thr | His | Gly | Gln | | His | Gly | Val | | |
| SEQ ID NO 19 Alloferon 8 | | | | | His | Gly | His | Gly | Val | His | Gly | | | |

TABLE 2-continued

Alloferon sequence homology

| | \multicolumn{14}{c}{peptide} |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| SEQ ID NO 20 Alloferon 9 | | Leu | Ala | Ser | Leu | His | Gly | Gln | | His | Gly | Val | | |
| SEQ ID NO 21 Gemagglutin 377-388 | His | Gly | Tyr | Thr | Ser | His | Gly | Ala | | His | Gly | Val | | |
| SEQ ID NO: 24 Consensus sequence | | | | | | His | Gly | | | His | Gly | | | |
| SEQ ID NO: 24 Structural formula | | | R1 | | | His | Gly | | X1 | His | Gly | | R2 | |

Patent of the RF U.S. Pat. No. 2,172,322 illustrates alloferons sequence without consensus sequence presentation, which makes it impossible to precisely estimate core-heart part of peptides and separate significant modifications from insignificant.

Resulting from the analysis, alloferon family can be divided into 3 families with consensus sequences:

SGHGQ-HGV (SEQ ID NO: 25), VSGHGQ-HGV (SEQ ID NO: 26), SGHGQ-HGV (SEQ ID NO: 25), which is substantiated with the given computer estimations (FIG. 1) of alloferon families peptides sequences.

Example 2. Peptide A1 Computer Modeling (Tertiary Structure Analysis)

To understand short peptides structure, it is possible to use computer modeling, allowing to estimate peptide structure in whole and its separate domains. In particular, we needed to estimate potential for creation of the present peptides complexes with $Zn^{++}$ ion. For this, computer modeling of A1 peptide with the following structure was performed: His-Val-Ser-His-Gly-Gln-His-Gly-Val-His-Gly (A1) (SEQ ID NO: 27). Simple A1 complex buildup with $Zn^{++}$ ion allows to demonstrate peptide loop formation, stabilized with coordinate bonds of histidine residues with $Zn^{++}$ ion.

A1 peptide computer modeling (FIGS. 2A and 2B) showed that short peptide forms relax loop, where $Zn^{++}$ ion can interact with histidine residues accessible for interaction. In this case, general polypeptide structure fits the possibility to form $Zn^{++}$ ion complex at least with three histidine residues in loci 1.6 and 9.

Figure 3A:
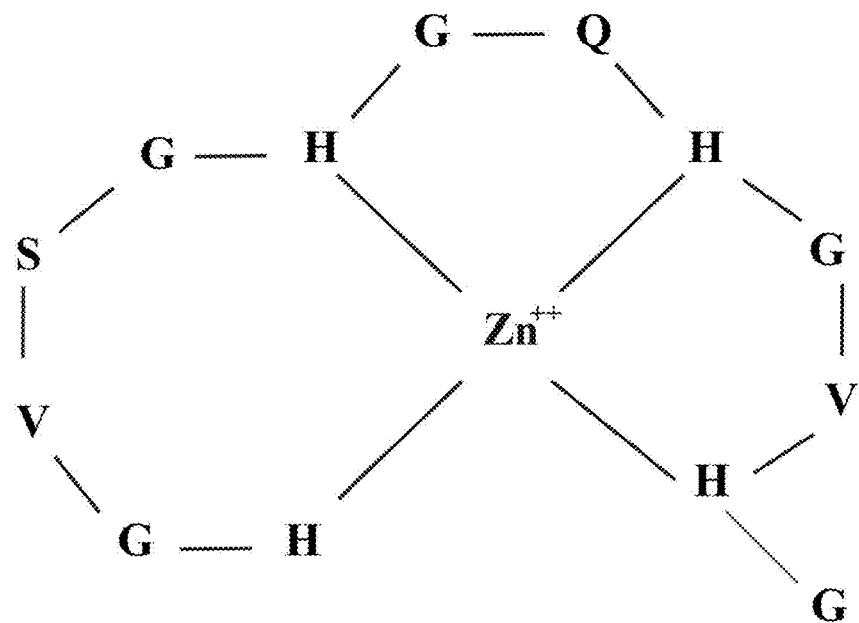
FIGS. 3A and 3B. Theoretical options of structures of A1 complexes with $Zn^{++}$ ion.
Figure 3B:
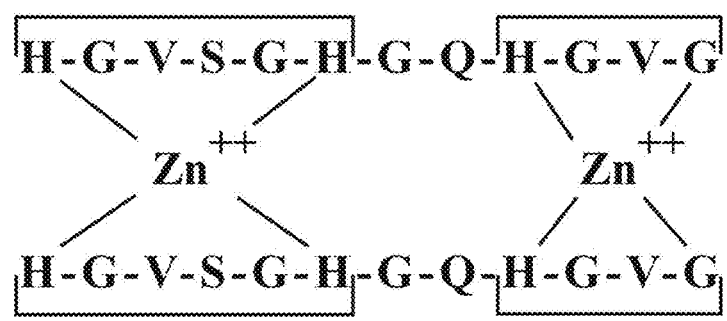

The simplified model (FIGS. 3A and 3B) Zn-A1 shows that significant portion of glycine residues is located in the N-end part of molecule. This corresponds to secondary structure of beta layers type. C-end part has alpha-helical structure with inside-exposed imidazole rings of histidine accessible for interaction with $Zn^{++}$ ion.

The Figure illustrates example with $Zn^{++}$. $Zn^{++}$ can be located virtually in any position.

A—intramolecular complex Zn-A1, organized as a loop.

A—intermolecular complex Zn-A1, organized as a dimer. Aggregation can be performed by adding new A1 molecules due to intermolecular fusion of $Zn^{++}$ ion in <<a>> and <<b>> regions or in the center of linear polypeptide with interaction of $Zn^{++}$ and histidine residues in positions 6 and 9.

Figure 2B:
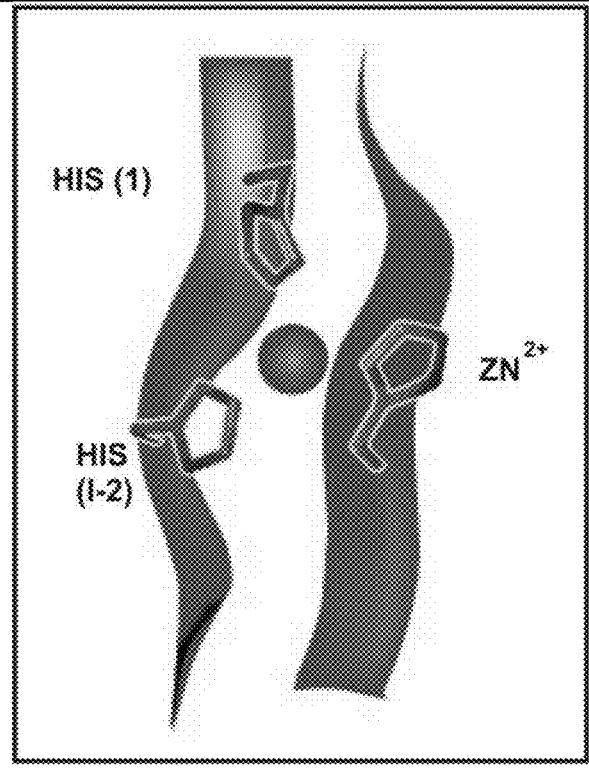

When analyzing A1 structure, high content and regular arrangement of histidine residues drives attention. FIGS. 2A and 2B show that A1 polypeptide forms almost perfect saddle-like structure. Histidine residues 1, 6 and 9 are most accessible for interaction with $Zn^{++}$ ion in this confirmation.

In this case significant conclusion can be made that complex formations with peptide excess comparing to $Zn^{++}$ can result in formation of intermolecular aggregates (FIG. 2B) Such structural transition fundamentally changes peptides properties making their structure, needed for bioactivity, compact, which was demonstrated in numerous studies [Rydengard V., Nordahl E. A., Schmidtchen A. Zinc potentiates the antibacterial effects of histidine-rich peptides against Enterococcus faecalis. FEBS Lett., 2006, Vol. 273, p. 2399-2406].

Example 3. Alloferon and its Closest Analogues are $Zn^{++}$-Binding Peptides $Zn^{++}$ ion binding with alloferon 1 (A1) and its homologs was studied by the method described [Shi Y., Beger R. D., Berg J. M. Metal binding properties of single amino acid deletion mutants of zinc finger peptides: studies using cobalt (II) as a spectroscopic prob. Biophys. J., 1993, Vol. 64, p. 749-753]. $Zn^{++}$ ion binding with A1 peptide was studied by the light-scattering method using ISS, Campaign, IL fluorimeter at 400 nm and excitation light 398 nm.

FIG. 4 shows graphs of $Zn^{++}$ ion interacting with A1 peptide.

For analysis conditions refer to Shi Y. et al. (1993)

A—(open circles) A1 and $Zn(NO_3)_2$. interaction Excess molar quantity of $Zn^{++}$ ion comparing to peptide was 1:10. Firm line—peptide enrichment with $Zn^+$ ion. Ground peptide mass changed into aggregates with complete enrichment. EDTA was added to aggregates. Subsequent to addition of EDTA the complex quickly dissociated and peptide (alloferon) changed to soluble phase.

FIG. 4 shows that $Zn^{++}$ ($Zn(NO_3)_2$ reacts with A1 peptide, resulting in exponential increase of light diffusion and followed by peptide aggregation in the form of polydisperse nanoparticles up to 50-60 nm in diameter followed by formation of suspending coarse aggregates. When adding EDTA chelating agent aggregates and A1 peptide complexes are dissolved.

In this wise, A1 peptide can react with $Zn^{++}$ ion forming soluble complexes at the first stage.

Example 4. Peptides React with $Zn^{++}$ Showing High Affinity with Nickel Adsorbents Chromatography at HiTrap columns showed that A1 acts as olygohistidine and has quite high affinity with the present adsorbent, and is completely eluted with imidazole solution. Elution was performed with gradient phosphate buffer/0.5 M imidazole (FIG. 5).

Example 5. Type I Interferons Induction

Type I interferons induction was studied by the previously published method [F. I. Yershov., O. I. Kiselev. Interferons and their inducers (from the molecule to the drug) M.: Publ. House. Geotar-Media, 2005-P. 356, Chernysh et al. 2002]. FIG. 6 shows findings for drug tests studying I type interferons induction ability. As may be inferred from the given data, Zn-A1 peptide had maximum interferon induction activity. Zn-A2 peptide was somewhat inferior. Nonmodified A1 peptide showed quite high level of interferon induction ability, but it was significantly inferior to derivatives in complex with $Zn^{++}$ ion and matched cycloferon activity.

Example 6 illustrates that these data correlate with protective action of drugs in case of nonsurvivable death grippal infection in mice.

Example 6. Antiviral Activity of the Experimental Lethal Grippal Pneumonia in White Mice, Induced with a Virus Influenza The model of lethal grippal infection of white scrub mice of both genders with weight 10-12 g from Rappolovo nursery was used for testing of peptide complexes antiviral activity. A/Aichi/2/68 (H3N2) flu strain has been used in the work, adapted to white mice in laboratory conditions with high pathogenicity, inducing infection with developing pneumonia and lethal outcome during 5-10 days depending on the viral dose.

Peptides and their derivatives were once administered abdominally to animals 6 and 12 hours before contamination in the amount of 1-2 µg/kg of animal weight. NSS or phosphate buffer in equal volume was placebo in control animal group.

Virus was previously titrated on animals and lethal concentration for mice has been determined. The animals were exposed to virus intranasally with slight ether anesthesia in the dose of 0.2 and 5 $LD_{50}$. Each study group comprised 10 mice. The animals were observed during 15 days, i.e. the term when 100% animal death is observed in experimental flu. Weight and death of animals was recorded day-to-day in control and experimental groups. Based on received mortality data, mortality rates in each group (number of died for 15 days animals to total amount of contaminated animals in the group ratio), protective index. The findings are represented in the FIG. 5. Analysis of findings showed that the action of studied drugs A1 relative to influenza A virus, pathogenic for mice was comparable to efficiency of the protective effect of reference drug Remantadin (80-87%—with dose of virus 1 $LD_{50}$). High protective effect of Zn-A1 complexes proves that formation of $Zn^{++}$ complex with A1 significantly potentiates type A1 peptides activity. Testing method, used in this case, proves that protective effect mainly should be attributed to interferon induction. The drug showed maximum activity when using in preventive scheme.

FIG. 7 shows protective effect of the studied drugs in lethal grippal infections of mice. Based on the above, we can state that the designed peptide has all the claimed properties.

Histidine-rich peptide complexes, primarily alloferon family peptides with $Zn^{++}$ ion, will make it possible to create drugs with directed mechanism of action and design them with regard to understanding of peptide properties and composition, and drug target structure.

What is claimed:

1. A peptide complex organized in three-dimensional structure and characterized by general structural formula:

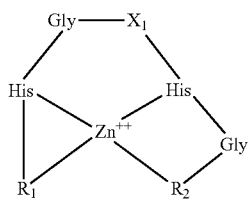

(SEQ ID NO: 29)

wherein:
- $X_1$ is selected from the group consisting of Gln, Ser, Asn, Val, Ala, Phe, and Asp or alternatively is absent; and
- $R_1$ and $R_2$ and comprise peptide chains that interact with transition metal ions, further wherein $R_1$ is selected from the group consisting of His-Gly-Val-Ser-Gly- (SEQ ID NO: 30), Cys-Val-Val-Thr-Gly- (SEQ ID NO: 31), Cys-Gly-, Val-Ser-Gly-, and His-Gly- or alternatively is absent; and $R_2$ is selected from the group consisting of: -Val-His-Gly, -Val-Phe-Val, -Val-His, and -Val-Asp or alternatively is absent, further wherein if $X_1$ is absent, $R_2$ must be present and if $R_2$ is absent, $X_1$ must be present.

2. The peptide complex according to claim 1, wherein said peptide complex induces interferon synthesis.

3. The peptide complex according to claim 1, wherein said peptide complex has antiviral activity.

4. The peptide complex according to claim 1, wherein $X_1$ is present and is selected from the group consisting of Gln, Ser, Asn, Val, Ala, Phe, and Asp.

5. The peptide complex according to claim 1, wherein $R_2$ is present and selected from the group consisting of: -Val-His-Gly, -Val-Phe-Val, -Val-His, and -Val-Asp.

6. The peptide complex according to claim 1, wherein $X_1$, $R_1$, and $R_2$ are all present.

7. The peptide complex according to claim 1, wherein the peptide component is 7 to 13 amino acid residues long.

8. The peptide complex according to claim 1, wherein $X_1$ is Gln, $R_1$ is His-Gly-Val-Ser-Gly- (SEQ ID NO: 30), and $R_2$ is -Val-His-Gly.

9. A peptide complex organized in three-dimensional structure and characterized by general structural formula:

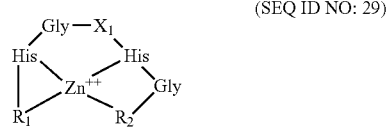

(SEQ ID NO: 29)

wherein:
- $X_1$ is selected from the group consisting of Gln, Ser, Asn, Val, Ala, Phe, and Asp or alternatively is absent; and
- $R_1$ and $R_2$ comprise peptide chains that interact with transition metal ions, further wherein $R_1$ is selected from the group consisting of: His-Gly-Val-Ser-Gly- (SEQ ID NO: 30), Cys-Val-Val-Thr-Gly- (SEQ ID NO: 31), Cys-Gly-, and Val-Ser-Gly-, or alternatively is absent; and $R_2$ is selected from the group consisting of: -Val-His-Gly, -Val-Phe-Val, -Val-His, and -Val-Asp or alternatively is absent.

* * * * *